United States Patent [19]

Steinmetz et al.

[11] Patent Number: 4,912,250

[45] Date of Patent: Mar. 27, 1990

[54] PROCESS FOR THE CO-PRODUCTION OF AROMATIC CARBOXYLATE AND ALKYL IODIDE

[75] Inventors: Guy R. Steinmetz; Mark Rule; Victor H. Agreda; Lanny C. Treece, all of Kingsport, Tenn.

[73] Assignee: Eastman Kodak Company, Rochester, N.Y.

[21] Appl. No.: 306,127

[22] Filed: Feb. 6, 1989

Related U.S. Application Data

[63] Continuation-in-part of Ser. No. 249,216, Sep. 26, 1988, abandoned, which is a continuation of Ser. No. 115,295, Nov. 2, 1987, abandoned.

[51] Int. Cl.$^4$ ............... C07C 67/36; C07C 17/22
[52] U.S. Cl. .................... 560/80; 560/97; 560/100; 560/102; 560/103; 570/181
[58] Field of Search ............ 560/97, 100, 80, 102, 560/103; 570/181

[56] References Cited

U.S. PATENT DOCUMENTS

| | | | |
|---|---|---|---|
| 2,565,462 | 8/1951 | Prichard et al. | 560/204 |
| 2,640,071 | 5/1953 | Leibu | 560/97 |
| 2,734,912 | 2/1956 | Leibu | 560/97 |
| 3,632,831 | 1/1972 | Knowles | 560/97 |

FOREIGN PATENT DOCUMENTS

87/03279A 6/1981 World Int. Prop. O. .

OTHER PUBLICATIONS

Nakayama et al., Bull. Chem. Soc. Japan, 42, No. 4 (Apr. 1969), 1124–1127.

Primary Examiner—Werren B. Lone
Assistant Examiner—Vera C. Clarke
Attorney, Agent, or Firm—Charles R. Martin; William P. Heath, Jr.

[57] ABSTRACT

Disclosed is a process for the co-production of an aromatic carboxylic esters and alkyl iodide by the carbonylation of an aromatic iodide in the absence of a Bronsted base and in the presence of an ether and a nickel catalyst.

12 Claims, No Drawings

PROCESS FOR THE CO-PRODUCTION OF AROMATIC CARBOXYLATE AND ALKYL IODIDE

This is a continuation-in-part of Ser. No. 249,216 filed Sept. 26, 1988, now abandoned, which is a continuation of Ser. No. 115,295 filed Nov. 2, 1987, now abandoned.

This invention relates to a novel carbonylation process for the preparation of both aromatic carboxylic esters and an iodine containing compound from which the iodine values can be economically recovered. The carbonylation is conducted in the presence of an ether and a catalytic amount of nickel.

The carbonylation of aromatic halides in the presence of nickel to obtain aromatic carboxylic acids and esters is well known in the art. Nakayama and Mizoroki (Bull. Chem. Soc. Japan 42 (1969) 1124) disclose the carbonylation of aromatic halides in the presence of an alcohol and a potassium acetate to produce the corresponding carboxylic acid ester.

While it is known that aromatic iodides can be carbonylated, the use of these materials has been discouraged by the cost associated with the difficulty of recovering the iodine values. For example, the use of basic materials in the carbonylation of aromatic halides, such as potassium acetate by Nakayama and Mizoroki, results in the formation of halide salts from which the halide values can be reclaimed only through uneconomical procedures involving severe chemical treatments.

In U.S. Pat. No. 2,565,462, Prichard and Tabet disclose the carbonylation of aromatic halides to aromatic carboxylic esters in the presence of alcohols, ethers, and phenols using nickel tetracarbonyl. However, only non-catalytic quantities of iron, nickel, and cobalt are used as promoters under reaction conditions of both temperature and pressure that are much more severe than is shown by our invention.

U.S. application Ser. No. 922,594, now abandoned, discloses the carbonylation of aromatic iodides to aromatic carboxylic esters and alkyl iodides in the presence of an alkanol and nickel. When alcohols are employed in reactions under typical carbonylation reaction conditions for aryl halides, water is a byproduct. Water can be formed in a number of different ways. For example, reaction of in situ generated hydrogen iodide with methanol results in the formation of methyl iodide and water. Alcohols can often dehydrate to their corresponding ether and water under typical carbonylation reaction conditions. The presence of water in the reaction mixture often leads to the production of a mixture of both carboxylic acids and esters. The presence of acid groups can present a purification problem if pure ester is desired as a polymer precursor.

We have discovered a process which not only results in the carbonylation of aromatic iodides to aromatic carboxylic esters with low acid content in excellent yields and at excellent rates of conversion but also results in production of alkyl iodides from which the iodine values can be economically recovered. In this invention, the carbonylation is conducted in the absence of a Bronsted base and in the presence of an ether and a catalytic amount of a nickel catalyst under aromatic carboxylic ester and alkyl iodide-forming conditions of temperature and pressure.

The advantages afforded by our invention are many. First, the iodine values in the alkyl iodide may be readily recovered by simply flashing the relatively volatile alkyl iodide from the mixture resulting from the carbonylation reaction. This can be accomplished either in the carbonylation reactor or, more preferably, in a pressure reduction vessel to which the mixture resulting from the carbonylation reaction is fed. Second, the object in feeding organic ethers is to minimize the amount of water in the carbonylation reactor which will reduce the acid content of the ester product. The ratio of aromatic acids to esters produced in the present invention is dependent on the concentration of water present in the carbonylation reactor. The capability of producing aromatic carboxylic esters with low acid content is both novel and useful. The low acid content allows for simpler and less expensive production and purification schemes and eliminates the need for an esterification step when esters are the desired product. Third, the carbonylation can be conducted at temperatures and pressures lower than that used in the prior art. Fourth, the reaction does not require a catalyst promoter which could complicate both the iodine and catalyst recycle.

The aromatic iodides which may be used in our process may be monoiodo or polyiodo e.g., di-, tri- and tetra-iodo aromatic compounds. The aromatic nucleus or moiety can contain from 6 to 18 carbon atoms, preferably 6 to 10 carbon atoms and may be carbocyclic aromatic such as benzene, biphenyl, terphenyl, naphthalene, anthracene, etc. In addition to one or more iodine atoms, the aromatic moiety may be substituted by various substituents substantially inert under the conditions employed in our process. Examples of such substituents include alkyl of up to about 12 carbon atoms such as methyl, ethyl, isobutyl, hexyl, 2-ethylhexyl, nonyl, decyl, dodecyl, etc.: cycloalkyl of about 5 to 12 carbon atoms such as cyclopentyl, cyclohexyl, 4-butylcyclohexyl, etc.; halogen such as chloro and bromo; alkoxycarbonyl of from 2 to about 8 carbon atoms such as methoxycarbonyl, ethoxycarbonyl, butoxycarbonyl, hexyloxycarbonyl, etc.; carboxyl; cyano; alkenyl of about 2 to 12 carbon atoms such as vinyl allyl, etc.; formyl; alkanoyl of about 2 to 8 carbon atoms such as acetyl, propionyl, butyryl, hexanoyl, etc.

Specific examples of the aromatic iodide reactants include iodobenzene, 1,3- and 1,4-diiodobenzene 1,3,5-triiodobenzene, 4-iodotoluene, 4-iodophenol, 4-iodoanisole, 4-iodoacetophenone, 4,4'-diiodobiphenyl, 4-chloroiodobenzene, 3-bromoiodobenzene and 2,6- and 2,7-diiodonaphthalene. Our process is particularly useful for the preparation of benzenedicarboxylic and naphthalenedicarboxylic esters with low acid content and thus the preferred reactants are diiodobenzenes, especially 1,3- and 1,4-diiodobenzene, and diiodonaphthalenes, especially 2,6- and 2,7-diiodonaphthalene.

The aromatic iodide reactants are known compounds and/or can be prepared according to published procedures. For example, T. Hudlicky et.al. *The Chemistry of Halides, Pseudohalides and Azides,* Supplement D, Part 2, 1142–1158, the disclosure of which is incorporated herein by reference in its entirety discloses a number of such processes. Another process described in J. Chem. Soc. 150 (1952) comprises treating an aromatic compound, such as benzene, with iodine in the presence of silver sulfate dissolved in concentrated sulfuric acid.

The ether used in the process of this invention, which is preferably dimethyl ether, results in the formation of methyl carboxylate esters, which may be used in transesterification reactions, and produces methyl iodide which is the most volatile of the alkyl iodides. However, other ethers containing up to about 12 carbon atoms, preferably up to about 4 carbon atoms, may be employed if desired. Examples of other suitable ethers include diethyl ether, dipropyl ether, dibutyl ether, dipentyl ether, dihexyl ether, diheptyl ether, dioctyl ether, didecyl ether, dibenzyl ether, dioxane, anisole, or mixed dialkyl ethers. Mixture of these ethers may also be employed. For each mole equivalent of aromatic ester produced, one mole of the ether is required.

The process provided by our invention can also be carried out in the presence of an organic co-solvent such as aliphatic, alicyclic and aromatic hydrocarbons, and halogenated hydrocarbons. Examples of such solvents include benzene, toluene, the xylenes, hexane, heptane, chlorobenzene, ethylene dichloride, methylchloroform, naphthalene, etc. However, the use of a co-solvent is not critical to the practice of this invention. Water or potential esterifying agents such as alcohols and their carboxylate esters may also be present in the reaction mixture depending upon the desired ester to acid ratio.

The nickel catalyst can be provided to the reaction medium as either nickel metal or as a number of simple nickel salts. Illustrative sources of nickel are nickel acetate, nickel chloride, nickel bromide, nickel iodide, nickel nitrate, nickel oxide, nickel acetylacetonate, nickel tetracarbonyl and its halogen substituted analogs. The amount of nickel is not significant as long as enough is present to catalyze the reaction. Preferably, the catalyst is present in a concentration of 10 to 0.001 mole percent, preferably 2.5 to 0.1 mole percent based on the moles of aromatic iodide reactant. Therefore, the total reaction medium has a catalyst concentration of about 10,000 ppm to 1 ppm with preferred catalyst concentrations of 2,500 to 100 ppm.

The carbonylation reaction is conducted in the presence of carbon monoxide, which is employed in amounts such that the total reaction pressure is suitable for the formation of both the aromatic carboxylic ester and the alkyl iodide. The carbon monoxide employed may be essentially pure or it may contain other gases such as carbon dioxide, hydrogen, methane and other compounds produced by synthesis gas plants. Normally, the carbon monoxide will be at least 90, preferably at least 95, percent pure.

The process of the present invention can be conducted at temperatures and pressures suitable for formation of both the aromatic carboxylic ester and alkyl iodide. The temperatures and pressures are interdependent and can vary considerably. Normally, the pressure will be at least 100 psig. While the process can be carried out at pressures as high as 10,000 psig, the cost of utilities and equipment required for such high pressure operation may not be commercially justified. Thus, the pressure normally will be in the range of about 125 to 4,000 psig, preferably about 300 to 1,500 psig. A particularly preferred pressure is 750 to 1,500 psig. A pressure of about 1,200 psig is often most desirable. While temperature as low as 125° C. and higher than 225° C. may be used, our process normally is carried out between about 150° and 275° C. The preferred temperature range is 180° to 250° C. A particularly preferred temperature is 220° C.

The relative amounts of carbon monoxide, ether and aromatic iodide and in our process can be varied substantially and are, in general, not critical. However, it is preferable to have at least stoichiometric amounts present relative to the aromatic iodide if complete conversion is desired.

When a polyiodo aromatic compound is used as the reactant in our carbonylation process, the products obtained include both aromatic polycarboxylic esters and partially carbonylated products such as iodoaromatic carboxylic esters. The latter compounds are useful as intermediates in the preparation of derivatives of aromatic carboxylic esters, for example, by displacement reactions whereby the iodo substituent is replaced with other radicals. The difunctional esters, such as dimethyl 2,6-naphthalenedicarboxylate, can be reacted with diols to produce high molecular weight polyesters suitable for molding plastics. Useful articles can be molded from these plastics, such as by injection molding. The relative amounts of partially or totally carbonylated products is highly dependent on the period of time that the reactant resides under carbonylation conditions.

The alkyl iodides prepared according to the process of our invention may be used in other chemical processes such as in the preparation of carboxylic acids and carboxylic anhydrides according to known carbonylation procedures. Alternatively, the alkyl iodide can be oxidatively decomposed at elevated temperature to produce a gaseous mixture of iodine, carbon dioxide, and water from which the iodine can be recovered. Alternatively, the alkyl iodides may be thermally decomposed to iodine and an alkane, or hydrogenated to hydrogen iodide and methane.

An important aspect of our invention is conducting the carbonylation in the absence of a Bronsted base. By the term Bronsted base we mean any substance that preferentially can act as a proton acceptor in the reaction medium and interfere with the formation of an alkyl iodide. In particular, the Bronsted base can be an acetate, formate, hydroxide, carbonate or alkoxide of an alkali, alkaline earth transition or non-transition metal. Examples of a Bronsted base are alkali metal carbonates, such as lithium carbonate, as well as alkali metal acetates such as lithium acetate, sodium acetate, potassium acetate and the like, preferably lithium acetate. Alkaline earth metal acetates, such as magnesium acetate, are also examples. Transition and nontransition metal acetates such as iron, manganese, zinc and tin acetates are further examples. Phosphines such as triphenylphosphine and amines such as pyridines and trialkylamines, for example triethylamine or trimethylamine are still further examples.

Our invention is further illustrated by the following examples. In the procedures utilized in the examples the materials employed are loaded into a 330 mL autoclave constructed of Hastelloy B2 alloy which is designed to operate in a rocking mode. The autoclave is pressurized with 200 psig carbon monoxide gas pressure at room temperature and then the gas is vented and the autoclave is sealed. In Examples 1–10, the autoclave is pressurized to 200 psig with carbon monoxide gas at ambient temperature and heated and rocked until reaction temperature was reached, at which time additional carbon monoxide gas is added to increase the autoclave internal pressure to the predetermined value. Reactor pressure is maintained by adding carbon monoxide at the same rate at which it is consumed by the reactants. The carbon monoxide used is essentially pure. When the predetermined reaction time is completed, the autoclave is cooled by a stream of cold air to approximately 25° C. After the gas is vented from the autoclave the crude product is isolated by filtration and analyzed by gas chromatographic methods. The % conversion is the mole percent of iodo-group converted to carboxylic acid or ester. The results are shown below.

| Example No. | 1 | 2 |
|---|---|---|
| Iodoaromatic wt (g) | 2,6-Diiodonaphthalene 30.0 | 2,6-Diiodonaphthalene 30.0 |
| Catalyst wt (g) | NiI$_2$.6H$_2$O 0.38 | NiI$_2$.6H$_2$O 0.38 |
| Ether vol (mL) | Dimethyl Ether 40.0 | Dimethyl Ether 40.0 |
| Co-Solvent wt (g) | Naphthalene 100.0 | 1-Methylnaphthalene 99.8 |
| Time (hour) | 2 | 1 |
| Pressure (psig) | 1,500 | 1,500 |
| Temp. (°C.) | 220 | 190 |
| % Conversion | 100 | 47.4 |

| Example No. | 3 | 5 |
|---|---|---|
| Iodoaromatic wt (g) | 2,6-Diiodonaphthalene 30.0 | 2,6-Diiodonaphthalene 30.0 |
| Catalyst wt (g) | NiI$_2$.6H$_2$O 0.38 | NiI$_2$.6H$_2$O 0.38 |
| Ether vol (mL) | Dimethyl Ether 40.0 | Dimethyl Ether 40.0 |
| Co-Solvent wt (g) | 1-Methylnaphthalene 100.2 | 1-Methylnaphthalene 99.9 |
| Time (hour) | 1 | 1 |
| Pressure (psig) | 1,500 | 1,500 |
| Temp. (°C.) | 205 | 245 |
| % Conversion | 85.3 | 96.1 |

| Example No. | 5 | 6 |
|---|---|---|
| Haloaromatic wt (g) | Bromobenzene 25.33 | Bromobenzene 25.08 |
| Ether vol (ml) | Dimethyl Ether 42.0 | Dimethyl Ether 42.0 |
| Co-Solvent wt (g) | 1-Methylnaphthalene 101.3 | 1-Methylnaphthalene 101.1 |
| Catalyst wt Ni (g) | NiI$_2$.6H$_2$O 0.12 | NiI$_2$.6H$_2$O 0.13 |
| Time (hour) | 1 | 1 |
| Pressure (psig) | 1,500 | 8,000 |
| Temp. (°C.) | 200 | 200 |
| % Conversion | 0.21 | 0.20 |
| Ester/Acid | 0 (only benzoic acid formed) | 0 (only benzoic acid formed) |

| Example No. | 7 | 8 |
|---|---|---|
| Haloaromatic wt (g) | 2,6-Diiodonaphthalene 30.02 | 2,6-Diiodonaphthalene 30.01 |
| Ether vol (ml) | Dimethyl Ether 42.0 | Dimethyl Ether 42.0 |
| Co-Solvent wt (g) | 1-Methylnaphthalene 100.91 | 1-Methylnaphthalene 100.42 |
| Catalyst wt Ni (g) | NiI$_2$.6H$_2$O 0.10 | NiI$_2$.6H$_2$O 0.10 |
| Time (hour) | 1 | 1 |
| Pressure (psig) | 1,500 | 8,000 |
| Temp. (°C.) | 200 | 200 |
| % Conversion | 64.7 | 18.7 |
| Ester/Acid | 15.3 | 8.1 |

| Example No. | 9 | 10 |
|---|---|---|
| Iodoaromatic wt (g) | 2,6-Diiodonaphthalene 30.0 | 2,6-Diiodonaphthalene 30.0 |
| Catalyst wt (g) | NiI$_2$.6H$_2$O 0.38 | NiI$_2$.6H$_2$O 0.38 |
| Ether vol (mL) | Dimethyl Ether 40.0 | Dimethyl Ether 40.0 |
| Co-Solvent wt (g) | 1-Methylnaphthalene 100.0 | 1-Methylnaphthalene 100.2 |
| Time (hour) | 1 | 1 |
| Pressure (psig) | 1,000 | 750 |
| Temp. (°C.) | 220 | 220 |
| % Conversion | 83.6 | 67.4 |

| Example No. | 11 | 12 |
|---|---|---|
| Iodoaromatic wt (g) | 2,6-Diiodonaphthalene 30.0 | 2,6-Diiodonaphthalene 30.0 |
| Catalyst wt (g) | NiI$_2$.6H$_2$O 0.38 | NiI$_2$.6H$_2$O 0.38 |
| Ether vol (mL) | Diethyl Ether 40.0 | Anisole 40.0 |
| Co-Solvent wt (g) | 1-Methylnaphthalene 100.2 | 1-Methylnaphthalene 99.7 |
| Time (hour) | 1 | 1 |
| Pressure (psig) | 1,500 | 1,500 |
| Temp. (°C.) | 220 | 220 |
| % Conversion | 96.2 | 33.4 |

While the invention has been described in detail with particular reference to preferred embodiments thereof, it will be understood that variations and modifications can be effected within the spirit and scope of the invention.

We claim:

1. A process comprising
   (1) co-production of an aromatic carboxylic ester and an alkyl iodide by carbonylating an aromatic iodide in the absence of a Bronsted base and in the presence of carbon monoxide, and ether and a catalytic amount of a catalyst consisting essentially of nickel under aromatic carboxylic ester and alkyl iodide-forming conditions of temperature and pressure, and
   (2) recovering the alkyl iodide.

2. The process of claim 1 wherein the aromatic iodide is selected from the group consisting of diiodonaphthalene and diiodobenzene.

3. The process of claim 2 wherein the diiodonaphthalene is 2,6-diiodonaphthalene and the diiodobenzene is 1,4-diiodobenzene.

4. The process of claim 1 wherein the ether contains from 1 to 4 carbon atoms.

5. The process of claim 4 wherein the ether is dimethyl ether.

6. The process of claim 1 wherein the temperature is in the range of about 150° to 275° C.

7. The process of claim 6 wherein the temperature is in the range of about 180° to 250° C.

8. The process of claim 1 wherein the pressure is in the range of 125 to 4,000 psig.

9. The process of claim 8 wherein the pressure is in the range of 300 to 1,500 psig.

10. The process of claim 1 wherein the process is carried out in the presence of an organic co-solvent.

11. A process comprising
   (1) co-production of an aromatic dicarboxylic ester selected from the group consisting of a dimethyl benzenedicarboxylate and a dimethyl naphthalenedicarboxylate and methyl iodide by carbonylating a diiodobenzene or a diiodonaphthalene in the absence of a Bronsted base and in the presence of carbon monoxide, dimethyl ether, an organic solvent and a catalyst consisting essentially of nickel at a temperature of about 180° to 250° C. and a pressure of about 500 to 1,500 psig, and (2) recovering the methyl iodide.

12. A process comprising (1) co-production of dimethyl 2,6-naphthalenedicarboxylate and methyl iodide which comprises carbonylating 2,6-diidonaphthalene in the absence of a Bronsted base and in the presence of carbon monoxide, dimethyl ether, an organic co-solvent and a catalyst consisting essentially of nickel at a temperature of about 220° C. and a pressure of about 1,200 psig, and (2) recovering the methyl iodide.

* * * * *